United States Patent [19]

Enjoji

[11] 4,387,721
[45] Jun. 14, 1983

[54] ULTRASONIC PROBE HAVING MEANS FOR RECEIVING A PUNCTURING CANNULA THERETHROUGH

[75] Inventor: Susumu Enjoji, Ootawara, Japan

[73] Assignee: Tokyo Shibaura Denki Kabushiki Kaisha, Kawasaki, Japan

[21] Appl. No.: 252,239

[22] Filed: Apr. 8, 1981

[30] Foreign Application Priority Data

May 30, 1980 [JP] Japan .................. 55-71539

[51] Int. Cl.³ ............................................. A61B 10/00
[52] U.S. Cl. ....................................... 128/660; 128/661
[58] Field of Search ................. 128/660, 661, 662, 663

[56] References Cited

U.S. PATENT DOCUMENTS

| 4,029,084 | 6/1977 | Soldner ................................. 128/2 |
| 4,108,165 | 8/1979 | Kopp et al. .......................... 128/2 |
| 4,289,139 | 9/1981 | Enjoji et al. ...................... 128/660 |

FOREIGN PATENT DOCUMENTS 2295727 7/1976 France ................................. 128/660

OTHER PUBLICATIONS

Whittingham, T. A., "A Multiple Transducer System for Heart, Abdominal and Obstetric Scanning"; 2nd European Congress on Ultrasonics in Medicine, May 1975; pp. 59–66.

Goldberg et al., "Ultrasonic Aspiration Biopsy Techniques", *Journal of Clinical Ultrasound*, vol. 4, No. 2, 1976.

Primary Examiner—Richard J. Apley
Assistant Examiner—G. Yanulis
Attorney, Agent, or Firm—Finnegan, Henderson, Farabow, Garrett & Dunner

[57] ABSTRACT

An ultrasonic probe having structure for receiving a puncturing cannula therethrough, the probe including a substantially rectangular parallelepiped-shaped support member, the height of the member being relatively much less than the length and width, a plurality of ultrasonic transducer elements arranged in at least one row closely adjacent to one edge of the bottom surface of the support member, cable structure for individually connecting said transducer elements to an external processing unit, and a slot for guiding the puncturing cannula, the slot opening into a first face of the parallelepiped-shaped member perpendicular to the bottom surface and adjoining said row of transducer elements, and said slot being centrally positioned relative to the row of transducer elements. Preferably the depth of the slot is only slightly greater than the diameter of the cannula and the width of the slot permits substantially no lateral movement of the cannula parallel to the row.

4 Claims, 3 Drawing Figures

ULTRASONIC PROBE HAVING MEANS FOR RECEIVING A PUNCTURING CANNULA THERETHROUGH

BACKGROUND OF THE INVENTION

This invention relates to an ultrasonic probe for use with a puncturing cannula and, more particularly, to an ultrasonic probe having a slot for guiding a puncturing cannula therethrough.

When withdrawing tissue or body fluids from organs in a human body such as liver or kidneys by a suitable puncturing cannula for diagnosis, it has been known to use an ultrasonic probe for guiding the cannula so as to perform a safe puncture by simultaneously observing on a display the objective of the operation, and the movement of the cannula in the body.

Shown in FIG. 1 is a conventional ultrasonic probe having means for receiving a puncturing cannula. The probe includes a substantially rectangular parallelepiped-shaped support member 1 provided with a plurality of ultrasonic transducer elements 2 arranged in at least one row on its bottom surface 1a which will be in contact with the human body. The transducer elements 2 are individually connected to a display (not shown) by a cable 3, as shown in FIG. 1, for showing tomographs of the organ to be contracted and the advancing cannula. The support member 1 is provided with a guide slot 4 extending through the support member 1 from the top surface 1b to the bottom surface 1a. The slot 4 narrows from the top surface 1b to the bottom surface 1a for guiding a cannula to position substantially at the midpoint of the row of transducer elements 2. The height of the member 1 between the surfaces 1a and 1b is normally greater than the width of the surface 1a, from front to back as shown.

An elongated aperture 5 communicating with the guide slot 4 is defined on a side face of the member 1 intersecting rectangularly with the bottom surface 1a and upper surface 1b of the support member 1. By this arrangement, when performing X-ray photography, after the cannula has punctured the objective of the subject, the support member 1 can be removed by a lateral movement on the body surface of the subject without disturbing the cannula.

Moreover, the conventional ultrasonic probe is constructed for use on the surface of the body and for use with a relatively long cannula. It has been found that in the conventional probe the cannula is unstable and difficult to direct with accuracy.

In recent years, the conventional ultrasonic probe has been used internally in examinations to identify, for example, metastasis of cancer of the liver. In these examinations, an incision is made in the abdomen and the probe is inserted into the abdomen and into actual contact with the liver and other organs which may be affected. In order to secure the proper alignment of the row of transducer elements 2 on the bottom surface 1a of the probe, a portion of the probe often must be inserted between the costae (ribs) and the liver or other organs.

Due to the height and weight of the conventional probe, undue pressure may be exerted not only on the organ under examination, but on other organs in contact with organs under examination.

SUMMARY OF THE INVENTION

It is accordingly an object of this invention to improve ultrasonic probes, wherein the ultrasonic probe can be used to perform a cannula puncture with greater stability and accuracy.

It is another object of this invention to provide an ultrasonic probe which can be used in physical contact with internal organs of the body, and at least partially beneath the ribs without undue pressure on the organ under examination or other organs in contact therewith.

Briefly, these and other objects are achieved in accordance with a first aspect of the invention, by constructing an ultrasonic probe having means for receiving a puncturing cannula therethrough, the probe comprising a substantially rectangular parallelepiped-shaped support member the height of said member being relatively much less than the length or width, a plurality of ultrasonic transducer elements arranged in at least one row closely adjacent to one edge of the bottom surface of the support member, cable means for individually connecting said transducer elements to an external processing unit, a slot for guiding the puncturing cannula, said slot opening into a first face of said parallelepiped-shaped member perpendicular to said bottom surface and adjoining said row of transducer elements and said slot being centrally positioned relative to said row of transducer elements.

DESCRIPTION OF THE PREFERRED EMBODIMENT

Figure 1:
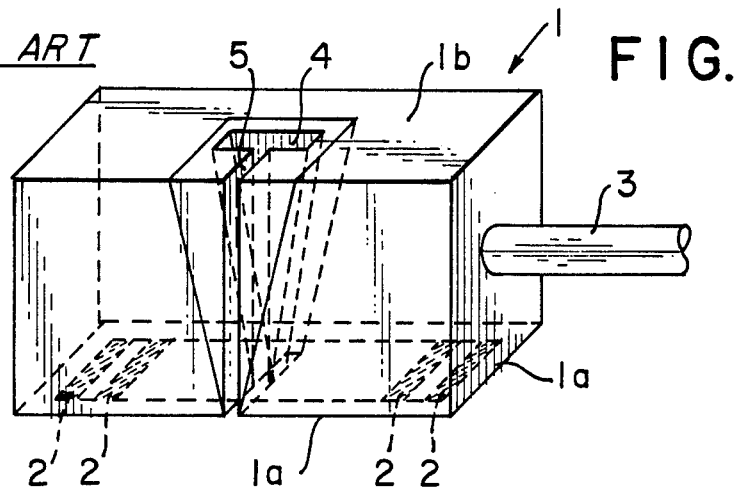
FIG. 1 is a schematic perspective view to illustrate an example of a conventional ultrasonic probe.
Figure 2:
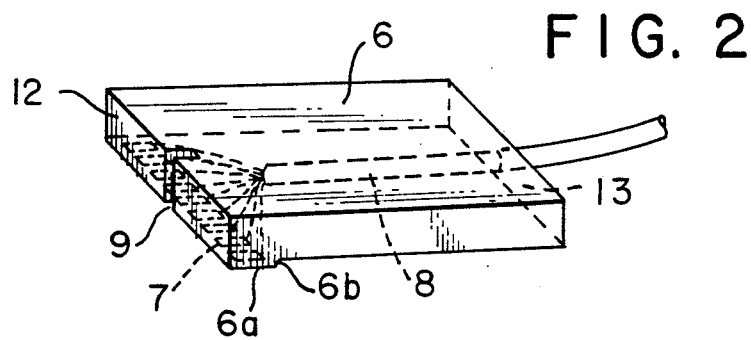
FIG. 2 is a schematic perspective view to illustrate an embodiment of the ultrasonic probe according to this invention.

Referring to FIG. 2, there is shown an ultrasonic probe according to the invention including a substantially rectangular support member 6 wherein the height is relatively much less than the length or width. Transducer elements 7 are arranged in at least one row on a portion 6a of the bottom surface of the support member 6. The portion 6a is positioned along one edge of the bottom surface and adjacent a face 12 of the support member 6, the face being perpendicular to the bottom surface and defining the height of the member.

Preferably, a major portion of the bottom surface of the support member 6 has been cut away in a shallow depth to form a shoulder 6b substantially parallel to the face 12, the portion 6a of the bottom surface lying between the shoulder 6b and the perpendicular face 12.

The transducer elements 7 are individually connected through a cable 8 to a display (not shown) through a suitable processing circuit (also not shown). The cable 8 preferably exits the member 6 through a face 13 of the parallelepiped-shaped support member 6 opposite the face 12 adjacent to the portion 6a containing the transducer elements 7. By means of the display, tomographs of the organ under examination, as well as the cannula, can be shown as the examination proceeds.

A slot 9 is cut into the face 12 perpendicular to the surface of the portion 6a and preferably at the midpoint of the row of transducer elements 7. The slot 9 is a groove opening into the face 12 and extending from the bottom portion 6a through the top surface of the support member 6, whereby a shortened cannula can be inserted into the slot substantially perpendicular to the bottom portion 6a in which the transducer elements are emplaced.

Preferably the ultrasonic member 6 is fabricated of synthetic resins.

According to the arrangement of the ultrasonic probe as defined above, the height of the probe is relatively quite low, and the guide slot shortened. The puncture by the cannula can, therefore, be performed with great accuracy and stability with a shortened cannula and without an area within which the cannula can be pointed in an arc laterally.

Figure 3:
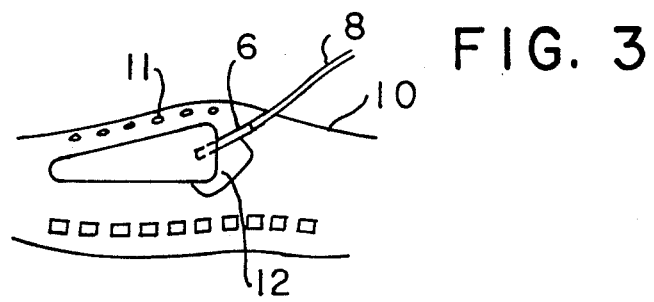
FIG. 3 is a schematic pictorial view to illustrate utilization of an ultrasonic probe according to the invention.

Likewise if, as shown in FIG. 3, a portion of the ultrasonic probe is inserted between the costae 11 and the liver 12 through an incision in the abdomen 10, the bottom surface portion 6a having thereon the transducer elements 7 of the ultrasonic probe shown in FIG. 2, would be in physical contact with the liver 12 or other organs as the case might be. Due to the reduced height of the support member 6, and the repositioning of the transducer elements 7 near the edge of the bottom surface of the support member, it is possible to manipulate the probe for proper alignment of the transducer elements relative to the objective, without placing undue pressure on the objective organs, or other organs in contact therewith.

Furthermore, by having the short guide slot 9 in the edge of the support member, it is feasible to locate the diseased portion of the liver, for example, by the tomography, puncture the liver at the diseased portion, and then withdraw the support member from around the cannula via the open slot without disturbing the cannula.

What is claimed is:

1. An ultrasonic probe for insertion substantially wholly into the human abdomen, and having means for receiving a puncturing cannula therethrough, the probe comprising:
    a substantially rectangular parallelepiped-shaped support member, the height of said member being relatively much less than the length or width, thus forming top and bottom surfaces of the member of much larger area than any other surfaces;
    a plurality of ultrasonic transducer elements arranged in at least one row in, and closely adjacent to one edge of, the bottom surface of the support member, said row extending substantially the length of said edge but being of relatively short width for occupying only a relatively small portion of said bottom surface;
    cable means for individually connecting said transducer elements to an external processing unit; and
    a narrow slot for guiding the puncturing cannula, said slot opening into a first face of said parallelepiped-shaped member perpendicular to said bottom surface and adjoining said row of transducer elements, said slot being centrally positioned relative to said row of transducer elements and permitting substantially no lateral movement of the cannula parallel to said row.

2. The probe of claim 1 wherein the depth of said slot is only slightly greater than the diameter of the cannula.

3. The probe of claim 2 wherein said cable is encapsulated in said member and extends outwardly therefrom through a second face of the member opposite from and parallel to said first face.

4. The probe of any one of claims 1, 2 and 3 wherein a relatively shallow portion of said bottom surface of said member has been cut away forming a shoulder substantially parallel to said first face, said row of transducer elements being positioned in the area formed between said shoulder and said first face, and said member substantially retaining its original shape.

* * * * *